(12) United States Patent
Slater

(10) Patent No.: US 6,442,994 B1
(45) Date of Patent: Sep. 3, 2002

(54) INSTRUMENT FOR COMBUSTIBLE GAS DETECTION

(75) Inventor: Cody Zane Slater, Calgary (CA)

(73) Assignee: BW Technologies Limited, Calgary (CA)

( * ) Notice: Subject to any disclaimer, the term of this patent is extended or adjusted under 35 U.S.C. 154(b) by 0 days.

(21) Appl. No.: 09/848,440

(22) Filed: May 3, 2001

(30) Foreign Application Priority Data

May 4, 2000 (GB) .............................................. 00/00787

(51) Int. Cl.⁷ .......................... G01N 33/497; F01N 3/10
(52) U.S. Cl. ...................................... 73/23.31; 422/174
(58) Field of Search .............................. 73/23.31, 23.2, 73/31.06; 422/174; 204/426; 436/141

(56) References Cited

U.S. PATENT DOCUMENTS

| | | | | |
|---|---|---|---|---|
| 3,960,495 A | * | 6/1976 | Tantram | 436/141 |
| 4,485,666 A | * | 12/1984 | Higgins et al. | 73/23.2 |
| 5,070,721 A | * | 12/1991 | Tantram | 73/23.31 |
| 5,767,388 A | * | 6/1998 | Fleischer et al. | 73/31.06 |
| 5,902,556 A | * | 5/1999 | Van De Vyver et al. | 422/174 |
| 6,009,742 A | * | 1/2000 | Balko | 73/23.31 |
| 6,238,536 B1 | * | 5/2001 | Lundgren et al. | 204/426 |

FOREIGN PATENT DOCUMENTS

| | | |
|---|---|---|
| GB | 2091882 | 8/1982 |
| GB | 2099154 | 12/1982 |
| GB | 2105849 | 3/1983 |
| GB | 2330438 | 4/1999 |

* cited by examiner

Primary Examiner—Daniel S. Larkin
(74) Attorney, Agent, or Firm—Michael B. McMurry

(57) ABSTRACT

A method for detecting combustible gases or vapours using a combustible gas sensor or pellistors includes the steps of keeping the combustible gas sensor or the pellistor beads inactive until an oxygen sensor indicates a variation from a reference level of oxygen, such variation representing the potential presence of combustible gases or vapours.

14 Claims, 1 Drawing Sheet

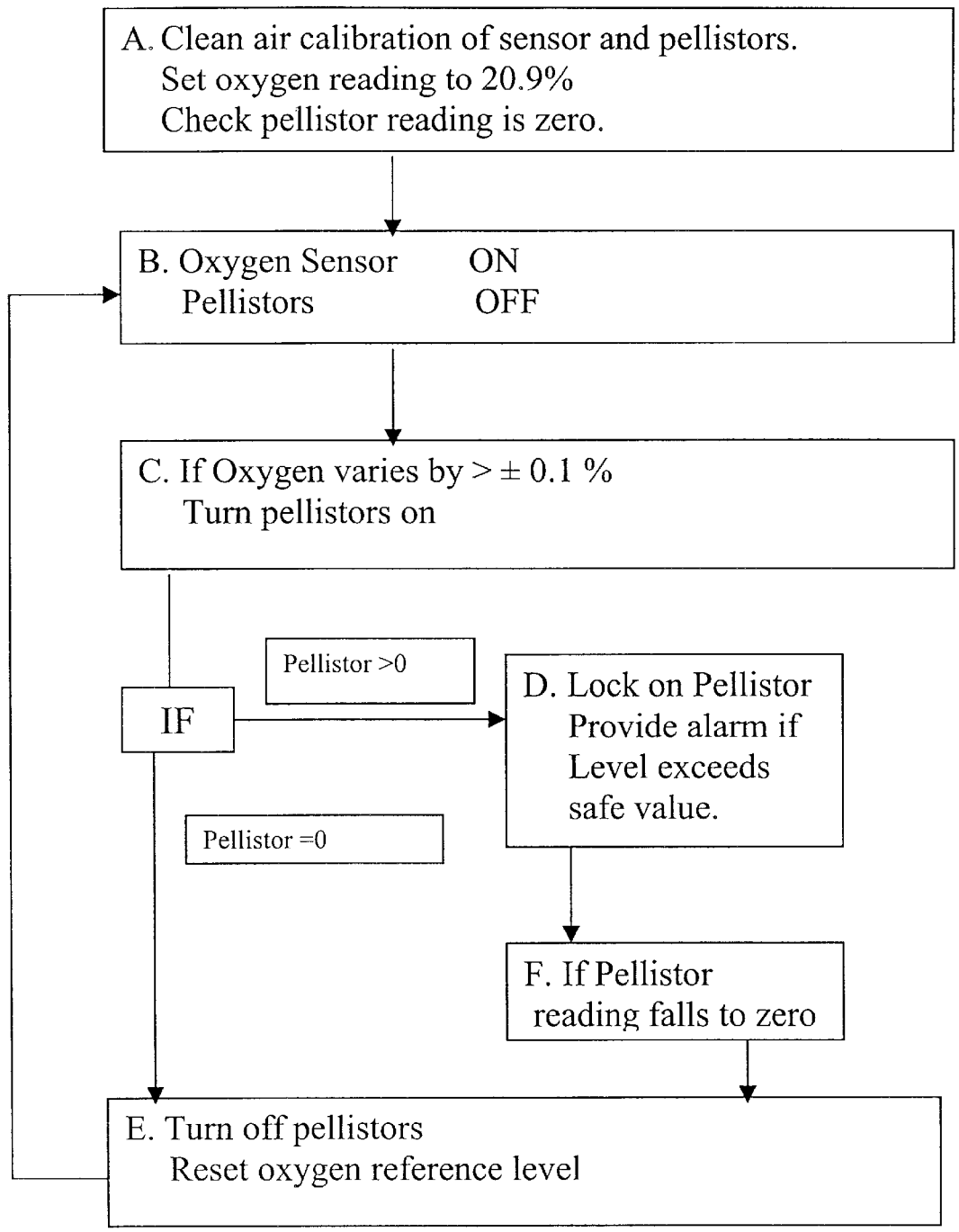

INSTRUMENT FOR COMBUSTIBLE GAS DETECTION

BACKGROUND OF THE INVENTION

Field of the Invention

This invention relates to an instrument and a method for the detection of combustible gases or vapours in air.

In particular, although not exclusively, the present invention has reference to catalytic bead sensors intended for such detection and also to the method of their usage. It is to be understood, however, that the invention also has reference to combustible gas sensors in general, for example metal oxide semiconductor type sensor, field effect transistor sensors and others.

Conventional catalytic bead sensors used for the detection of combustible gases of vapours in air incorporate an electrically heated platinum coil embedded within a detector bead comprising a porous ceramic support containing a suitable catalyst component impregnated within its pores. At an appropriate temperature the gas or vapour to be measured reacts (combusts) with oxygen from the air at the catalyst surface within the bead. Heat evolved by this reaction increases the temperature of the bead and consequently the electrical resistance of the platinum coil embedded within the bead. This change in resistance provides a measure of the amount of combustible gas or vapour in the atmosphere under test.

In a complete device, a second compensator bead is also employed to compensate for changes in ambient conditions such as temperature, humidity etc., which could provide erroneous readings. The compensator bead is rendered inactive to the combustion reaction but being in all other respects closely similar in structure to the detector bead, it responds similarly to ambient conditions such as temperature, humidity etc and its output can therefore be used to subtract any such extraneous effects from the signal obtained from the detector bead. The matched pair of detecting and compensating beads is conveniently employed in a Wheatstone Bridge measurement circuit providing a signal which is proportional to the concentration of combustible gas or vapour in the atmosphere under test. The detector and compensator beads are known as pellistors, see E. Jones, 'The Pellistor Catalytic Gas Detector' in 'Solid State Gas Sensors', edited by P. T. Moseley and B. C. Tofield, 1987 (ISBN 0-85274-514-1).

A problem which can arise with known pellistor bead devices is that they can be poisoned by certain gases or vapours to which the detector bead may be exposed, see S. J. Gentry & P. T. Walsh, 'The Theory of Poisoning of Catalytic Flammable Gas-sensing Elements', in Solid State Gas Sensors, edited by P. T. Moseley and B. C. Tofield, 1987 (ISBN 0-85274-514-1). The poison resistance of a conventional catalytic bead detector largely depends upon the surface area of catalyst within the bead. When poisons such as silicone vapours access the heated catalyst surface it is thought that the silicones adsorb on the catalyst surface where they decompose thermally to silica which forms an overlayer which progressively blocks the active catalyst sites. As this process continues the signal from the element decreases until the element is rendered inactive to combustible gases such as methane. This process is irreversible.

Other gases such as hydrogen sulphide also reduce the output from pellistor detector beads by being thermally decomposed on the catalyst surface to form blocking films (such as sulphur or solid sulphides) but in these instances the process can be reversed by raising the temperature of the element temporarily to drive off the blocking film; these substances are therefore referred to as inhibitors rather than poisons. Nevertheless their effects are detrimental to the instrument operation and especially if the circumstances are such that it is not possible to increase the detector bead temperature to reactivate the bead, for example if the degree of inhibition is very significant during use in a duty period before it is subjected to a recalibration.

Another drawback with the use of pellistor devices, particularly with portable instrument operation, is that the pair of matched detector/compensator beads requires power to maintain the temperature of the beads. Typical bead temperatures of conventional devices for methane detection are about 500 degrees centigrade and power requirements are around 150 to 200 mW per bead (0.3 to 0.4 watts per matched pair). Some larger beads designed for use where poison resistance is of major importance have even greater power requirements, up to 1.2 watts per pair. The latter are not normally used in portable applications but even the lower power sensors have substantial battery requirements in portable instruments.

SUMMARY OF THE INVENTION

An object of the present invention is to provide an improved method and an instrument for the detection of combustible gases or vapours in air.

According to a first aspect of the invention, a method for the detection of combustible gases or vapours in an atmosphere using a sensor, includes the steps of exposing the sensor to the atmosphere, sensing the atmosphere for the level of oxygen, activating the sensor responsive to a predetermined level of oxygen change indicating the presence of a contaminant gas or vapour, detecting the level of combustible gases or vapours in the atmosphere using the sensor, and maintaining the activation of the sensor or deactivating the sensor dependent upon the level of contaminant gases of vapours detected.

According to a second aspect of the invention a method for the detection of combustible gases or vapours in an atmosphere using pellistors comprising a detector bead and a compensator bead, includes the steps of exposing the pellistor to the atmosphere, sensing the atmosphere for the level of oxygen, activating the pellistors responsive to a predetermined level of oxygen change indicating the presence of a contaminant gas or vapour, detecting the level of combustible gases or vapours in the atmosphere using the pellistors, and maintaining activation of the pellistor or deactivating the pellistors dependent upon the level of contaminant gases or vapours detected.

The activation of the sensor or the pellistors may be on a continuous basis or cyclical on an on/off basis.

According to a further aspect of the invention an instrument for the detection of combustible gases or vapours in an atmosphere, includes a sensor for the combustible gas, an oxygen sensor adapted to sense a change in the level of oxygen in the atmosphere, and control means for controlling the activation of the sensor responsive to the sensed level of oxygen in the atmosphere falling below a predetermined reference level of oxygen.

According to a further aspect of the invention an instrument for the detection of combustible gases or vapours in an atmosphere, includes pellistors comprising a detector bead and a compensator bead, an oxygen sensor adapted to sense a change in the level of oxygen in the atmosphere, and control means for controlling activation of the pellistors responsive to the sensed level of oxygen in the atmosphere falling below a predetermined reference oxygen level.

The control means or other means may be adapted to effect activation and to maintain activation of the sensor or pellistors on a continuous basis or on a cyclic on/off basis in the event that combustible gas is detected.

The instrument is provided with a power source which may be mains or battery operated.

The oxygen sensor may be an electrochemical oxygen sensor which is self-powered, for example of a type described in UK Patent 1 571 282. The oxygen sensor may be maintained constantly in an active mode, there being little power consumption attributable to this activity.

In clean dry air, the oxygen sensor provides a reference reading equivalent to 20.9% oxygen. When any other substance is present it dilutes the ambient oxygen below the predetermined reference level and produces a reaction in the oxygen sensor output. The change in oxygen reading triggers the instrument to activate the pellistor to determine whether the change is due to the presence of a combustible substance. By virtue of the invention the pellistor is only activated when the presence of a combustible substance is suspected. Accordingly the instrument power requirements and the poisoning/inhibition rate of the pellistor beads are greatly reduced.

For example, the Lower Explosive Limit (LEL) for methane in air is 5% methane and instruments are required to give an alarm at about 10 to 25% of the LEL level (i.e. 0.5 to 1.25% methane), depending on the application. In clean dry air the oxygen sensor's output would correspond to the present reference point equivalent to an oxygen concentration of 20.9%. The presence of 0.5% methane will displace the oxygen concentration to 0.995 of the clean air value (20.9×0.995=20.8% oxygen), a reduction in the electrochemical sensor output equivalent to 0.1% oxygen. Thus in an application requiring a 10% methane LEL alarm, the instrument could be designed to switch on the pellistor only when the oxygen sensor output deviated by more than 0.1% oxygen equivalent below its present reference point. If the pellistor then confirmed the presence of combustible gas it would be kept on and an alarm provided if the indicated level were at or above 0.5% methane. Similarly, if a 25% methane LEL alarm level were required, the pellistor could be turned on when the oxygen sensor output reduced by more than 0.25% oxygen equivalent concentration below its present reference point and an alarm produced if the pellistor indicated combustible gas concentration at or above 1.25% methane.

The oxygen sensor may also vary with other parameters such as the ambient pressure, temperature, humidity or the presence of other, noncombustible gases which need to be taken into account with a practical instrument. For electrochemical oxygen sensors employing a gas phase controlling diffusion barrier the ambient pressure and temperature coefficients are relatively small (see, B. S Hobbs, A. D. S. Tantram, R Chan-Henry, 'Liquid Electrolyte Fuel Cells', in Techniques and Mechanisms in Gas Sensing' edited by P. T. Moseley, J. O. W. Norris and D. E. Williams, 1991 (ISBNo-7503-0074-4). Theoretically, the pressure coefficient is zero and the temperature coefficient 0.17% per centigrade degree change. Somewhat greater values are experienced in practice but with these types of oxygen sensors, pressure corrections are negligible and temperature corrections, although necessary are small and easily accomplished accurately. Other types of oxygen sensor can be employed such as the solid membrane type although the temperature and pressure compensations would be significantly greater and more difficult to make as accurately.

Water vapour (humidity) and other non-combustible gases which may be present will depress the oxygen concentration (and hence the oxygen sensor output) to a similar extent to a combustible gas at the same concentration. For example, at 20° C., air saturated with water vapour (100% relative humidity) contains about 2.3% water and relative to dry air at the same temperature the oxygen level will be reduced from 20.9% to 20.4%. At higher temperatures the concentrations of water in air at the same relative humidities will be greater. Thus, for example, at 40° C. air at 100% relative humidity contains about 7.3% water vapour and the oxygen concentration depresses to about 19.4% compared to 20.9% for dry air at the same temperature.

The present invention caters for such variations in the oxygen sensor output with non-combustible components in the air (particularly water vapour) and/or any inaccuracies in the temperature compensation circuitry by the method shown by way of example in the flow chart of the accompanying drawing which shows the operation steps of the invention.

BRIEF DESCRIPTION OF THE DRAWING

By way of example the a method for the detection of combustible gases or vapours in air according to the invention is described below with reference to the accompanying drawing which is block diagram representing the instrument and the steps of the said method.

DETAILED DESCRIPTION OF THE PREFERRED EMBODIMENT

Referring to the drawing, in Box A the instrument of the present invention is first calibrated in clean, dry air and the oxygen sensor reference is set equivalent to 20.9% oxygen. The pellistors are also calibrated using for example an air/methane mixture of known methane concentration. It is also possible to calibrate the activated pellistors and set the oxygen sensor reference point using a single dry calibration gas of known oxygen and methane concentrations.

Box B shows the pellistors de-activated with the oxygen sensor in an active mode. In this condition, the instrument is ready for use.

Box C depicts a situation in which the oxygen sensor output varies by more than ±0.1% oxygen equivalent, namely for a 10% methane LEL alarm instrument. If the output varies to this extent, the pellistors are activated for a preset minimum period to allow sufficient time for them to become fully operational.

In Box D, if the pellistors indicate the presence of a combustible gas or vapour, then they will provide a measure of the combustible gas or vapour. If the indicated level is or becomes equal to or greater than the preset alarm level, e.g. methane greater than 10% LEL (greater than 0.5% methane) the instrument will give a suitable alarm. In this case, a minimum level at which the instrument locks on the pellistors will be preset to allow for any baseline variations of the pellistors, below which level of combustible gas concentration it would not be required to maintain the pellistors active.

Box E shows the situation in which the pellistors do not indicate the presence of any significant concentrations of combustible gas resulting from the change in oxygen level. In this instance, the instrument deactivates the pellistors and resets the oxygen reference level to the current value and the instrument operation continues from Box B.

Box F represents the step taken in the event that the pellistor reading falls to zero or an acceptably safe level following on from Box D.

It will be understood that the various operational steps indicated in the diagram may conveniently be carried out using a suitable microprocessor control. Alternative and equivalent forms of control may equally well be employed in combination with the instrument.

The use of a cycling on/off control for the sensor or pellistors will be understood to have a power conservation advantage while not compromising the efficacy of the instrument.

As an alternative to the compensator bead a fixed resistor circuit may be employed and accordingly the invention embraces the use of a detector bead in combination with such a fixed resistor circuit.

The present invention thus provides an improved method and instrument for detecting combustible gases and vapours having the advantage of reducing power requirements and reducing the poisoning/inhibition effect, thereby prolonging the potential life of the instrument.

I claim:

1. A method for the detection of combustible gases or vapours in an atmosphere using a sensor, includes the steps of exposing the sensor to the atmosphere, sensing the atmosphere for the level of oxygen, activating the sensor responsive to a predetermined level of oxygen change indicating the presence of a contaminant gas or vapour, detecting the level of combustible gases or vapours in the atmosphere using the sensor, and maintaining the activation of the sensor or deactivating the sensor dependent upon the level of contaminant gases of vapours detected.

2. A method for the detection of combustible gases or vapours in an atmosphere using pellistors comprising, including the steps of exposing the pellistors to the atmosphere, sensing the atmosphere for the level of oxygen using an oxygen sensor, activating the pellistors responsive to a predetermined level of oxygen change indicating the presence of a contaminant gas or vapour, detecting the level of combustible gases or vapours in the atmosphere using the pellistors, and maintaining activation of the pellistors or deactivating the pellistors dependent upon the level of contaminant gases or vapours detected.

3. A method according to claim 2 in which the combustible gas sensor, the pellistors and the oxygen sensor are pre-calibrated.

4. A method according to claim 1 in which the oxygen sensor is calibrated to a predetermined level a variation from which is adapted to activate the combustible gas sensor or pellistors.

5. A method according to claim 1 in which the combustible gas sensor is or the pellistors are calibrated to remain activated upon the contamination by a combustible gas or vapour attaining or exceeding a predetermined level.

6. A method according to claim 1 in which the activation of the combustible gas sensor or the pellistors is continuous or cyclic on an on/off basis.

7. A method according to claim 4 which the sensor is adapted to provide an alarm when the predetermined level of combustible gas or vapour is exceeded.

8. A method according to claim 5 in which the pellistors are adapted to provide an alarm when the predetermined level of combustible gas or vapour is exceeded.

9. An instrument for the detection of combustible gases or vapours in an atmosphere, includes a sensor for detecting the combustible gas or vapour, an oxygen sensor adapted to sense a change in the level of oxygen in the atmosphere, and control means for controlling the activation of the combustible gas sensor responsive to the sensed level of oxygen in the atmosphere falling below a predetermined reference level of oxygen.

10. An instrument for the detection of combustible gases or vapours in an atmosphere including pellistors comprising a detector bead and a compensator bead, an oxygen sensor adapted to sense a change in the level of oxygen in the atmosphere, and control means for controlling activation of the pellistors responsive to the sensed level of oxygen in the atmosphere falling below a predetermined reference oxygen level.

11. An instrument according to claim 8 in which there is provided a power source.

12. An instrument according to claim 8 in which the oxygen sensor is an electrochemical oxygen sensor.

13. An instrument according to claim 11 in which when the instrument is in use the oxygen sensor is maintained constantly in an active mode.

14. An instrument according to claim 8 in which the control means is a microprocessor.

* * * * *